United States Patent [19]
Laughlin et al.

[11] Patent Number: 5,470,839
[45] Date of Patent: Nov. 28, 1995

[54] ENTERAL DIET AND METHOD FOR PROVIDING NUTRITION TO A DIABETIC

[75] Inventors: Philip Laughlin, Winnetka; John Alexander, Kenilworth; A. Reza Kamarei, Wilmette; Robert P. Dobbie, Lincolnshire, all of Ill.; Paul Lin, Fullerton, Calif.; Shen-Youn Chang, Wadsworth, Ill.; Sekhar Reddy, New Milford, Conn.; Etienne Grasset, Boulogne-Billancourt, France; Christian Melin, Winnetka, Ill.

[73] Assignee: Clintec Nutrition Company, Deerfield, Ill.

[21] Appl. No.: 271,114

[22] Filed: Jul. 6, 1994

Related U.S. Application Data

[63] Continuation-in-part of Ser. No. 51,632, Apr. 22, 1993, abandoned.

[51] Int. Cl.$^6$ .................................................. A61K 31/00
[52] U.S. Cl. ........................... 514/53; 426/810; 514/552; 514/866
[58] Field of Search ........................... 514/53, 552, 866; 426/810

[56] References Cited

U.S. PATENT DOCUMENTS

| | | | |
|---|---|---|---|
| 962,753 | 6/1910 | Fischer et al. | 530/366 |
| 1,027,844 | 5/1912 | Hoering | 514/866 |
| 2,194,188 | 3/1940 | Supplee | 167/81 |
| 2,937,974 | 5/1960 | Ferguson, Jr. | 167/58 |
| 3,698,912 | 10/1972 | Winitz | 426/810 |
| 3,699,219 | 10/1972 | Carlson, Jr. | 424/442 |
| 3,873,720 | 3/1975 | Suzuki et al. | 424/442 |
| 3,920,838 | 11/1975 | Flatt et al. | 424/319 |
| 4,053,589 | 10/1977 | Gans et al. | 424/319 |
| 4,202,888 | 5/1980 | Eckert et al. | 536/7 |
| 4,407,821 | 10/1983 | Mendy | 424/312 |
| 4,438,144 | 3/1984 | Blackburn | 424/319 |
| 4,497,800 | 2/1985 | Larson et al. | 426/74 |
| 4,528,197 | 7/1985 | Blackburn | 514/552 |
| 4,604,286 | 8/1986 | Kawajiri | 514/23 |
| 4,670,261 | 6/1987 | Samejima et al. | 514/23 |
| 4,670,286 | 6/1987 | Mahmoud | 426/72 |
| 4,678,807 | 7/1987 | Cotter et al. | 514/552 |
| 4,687,782 | 8/1987 | Brantman | 426/810 |
| 4,690,820 | 9/1987 | Simko | 426/810 |
| 4,703,062 | 10/1987 | Blackburn et al. | 514/552 |
| 4,711,953 | 12/1987 | Roger et al. | 530/364 |
| 4,753,963 | 6/1988 | Jandacek et al. | 514/552 |
| 4,810,726 | 3/1989 | Bistrian et al. | 514/552 |
| 4,847,296 | 7/1989 | Babayan et al. | 514/552 |
| 4,871,768 | 10/1989 | Bistrian et al. | 514/547 |
| 4,906,664 | 3/1990 | Bistrian et al. | 514/552 |
| 4,921,877 | 5/1990 | Cashmere et al. | 514/866 |
| 5,116,189 | 11/1992 | Trimbo et al. | 514/2 |
| 5,116,819 | 5/1992 | Trimbo et al. | 514/21 |
| 5,231,085 | 7/1993 | Alexander et al. | 514/49 |
| 5,292,723 | 3/1994 | Audry et al. | 514/23 |

FOREIGN PATENT DOCUMENTS

| | | |
|---|---|---|
| 189160 | 7/1986 | European Pat. Off. |
| 246747 | 11/1987 | European Pat. Off. |
| 265772 | 5/1988 | European Pat. Off. |
| WO86/07262 | 12/1986 | WIPO |

OTHER PUBLICATIONS

Bach et al., "Medium–Chain Triglycerides: An Update", *The American Journal of Clinical Nutrition*, vol. 36: Nov. 1982, pp. 950–962.

Vigen K. Babayan, "Speciality Lipids and Their Biofunctionality", *Lipids*, vol. 22, No. 6, 1987, pp. 417–420.

M. Wicklmayr et al., "Comparison of Metabolic Clearance Rates of MCT/LCT and LCT Emulsions of Diabetics", *Journal of Parenteral and Enteral Nutrition*, vol. 2, No. 1, 1988, pp. 68–71.

Sachiko Takase et al., "Possible Role of Insulin Status in the Increased Lipogenic Enzyme Activity by Dietary Medium–Chain Triglyceride in Rat Liver", *J. Nutr. Sci. Vitaminol.*, vol. 33, 1987, pp. 177–184.

Mitsuyoshi, "Effect of Medium–Chain Triglycerides (MCT) as an Energy Substrate After Hepatectomy in Rats with Streptozotocin–Induced Diabetes", *Res. Exp. Med.*, vol. 190, 1990, pp. 153–162.

Eric P. Bass, "Urinary Organic Acid Excretion During Feeding of Medium–Chain or Long–Chain Triglyceride Diets in Patients with Non–Insulin–Dependent Diabetes Mellictus", *Am. J. Clin. Nutr.*, vol. 52, 1990, pp. 923–926.

Robert H. Eckel et al., "Dietary Substitution of Medium–Chain Triglycerides Improves Insulin–Mediated Glucose Metabolism in NIDDM Subjects", *Diabetes*, vol. 41, May 1992, pp. 641–647.

Kathy Traianedes et al., "A High–Fat Diet Worsens Metabolic Control in Streptozotocin–Treated Rats by Increasing Hepatic Glucose Production", *Metabolism* vol. 41, No. 8, Aug. 1992, pp. 846–850.

Anderson, J. W. et al. "Dietary Fiber and Diabetes: A Comprehensive Review and Practical Application" in *Journal of the American Medical Association*, Sep. 1987, vol. 87, No. 9, pp. 1189–1197.

Anderson, J. W. "Fiber and Health: An Overview" in *Nutrition Today*, Nov./Dec. 1986, pp. 22–26.

Anderson, J. W. et al. "Metabolic Effects of High–Carbohydrate, High–Fiber Diets for Insulin–Dependent Diabetic Individuals" in *Am J Clin Nutr*, 1991, pp. 936–943.

(List continued on next page.)

*Primary Examiner*—Ronald W. Griffin
*Attorney, Agent, or Firm*—Hill, Steadman & Simpson

[57] ABSTRACT

A composition and method for providing nutrition, or a nutritional supplement, to a diabetic patient. Pursuant to the present invention, a low carbohydrate, high fat enteral formulation is provided. The fat comprises, in part, medium chain triglycerides (MCTs). Preferably, the composition includes a high percent of mono-unsaturated fats, high amylose starch, and soluble dietary fiber.

20 Claims, No Drawings

OTHER PUBLICATIONS

Anderson, J. W. et al. "Nutritional Management of Diabetes Mellitus" in *Modern Nutrition in Health and Disease*, M. E. Shils, ed., Lee and Febiger, 1994, pp. 1259–1285.

Behall, Kay M. et al. "Diets Containing High Amylose vs. Amylopectic Starch: Effects on Metabolic Variables in Human Subjects" in *Am J Clin Nutr*, 1989, pp. 337–344.

Behall, Kay M. et al. "Effect of Long–term Consumption of Amylose vs. Amylopectin Starch on Metabolic Variables in Human Subjects" in *Am J Clin Nutr*, 1995 pp. 334–340.

Behall, Kay M. et al. "Effect of Starch Structure on Glucose and Insulin Responses in Adults" in *Am J Clin Nutr*, 1988, pp. 428–432.

Blackburn, Nigel A. et al. "The Influence of Guar Gum on the Movements of Inulin, Glucose and Fluid in Rat Intestine During Perfusion in vivo" in *Pflügers Archiv*, 1983, pp. 144–148.

"Consensus Development Conference on Diet and Exercise in Non–Insulin–Dependent Diabetes Mellitus" in *Diabetes Care* by National Institutes of Health, Sep.–Oct. 1987, pp. 639–644.

Coulston, Ann et al. "Effect of Differences in Source of Dietary Carbohydrate on Plasma Glucose and Insulin Responses to Meals in Patients with Impaired Carbohydrate Tolerance," in *The American Journal of Clinical Nutrition*, 1981, pp. 2716–2720.

Crapo, Phyllis A. et al. "Postprandial Plasma–glucose and –insulin Responses to Different Complex Carbohydrates" in *Diabetes*, vol. 26, pp. 1178–1183 Dec. 1977.

Crapo, Phyllis A. "Simple Versus Complex Carbohydrate Use in the Diabetic Unit," in *Ann. Rev. Nutr.*, 1985, pp. 95–114.

Cummings, John H. "The Role of Dietary Fibre in the Human Colon," in *CMA Journal*, Dec. 6, 1980, pp. 1109–1114.

Garg, Abhimanyu et al. "Comparison of a High–Carbohydrate Diet with a High Monounsaturated–Fat Diet in Patients with Non–Insulin Dependent Diabetes Mellitus" in *N Engl J Med*, Sep. 29, 1988, pp. 829–834.

Goda, Toshinao et al. "Effect of High–Amylose Starch on Carbohydrate Digestive Capability and Lipogenesis in Epididymal Adipose Tissue and Liver of Rats" in *J. Nutr. Biochem.*, May, 1994, pp. 256–260.

Goddard, Mary S. "The Effect of Amylose Content on Insulin and Glucose Responses to Ingested Rice" in *The American Journal of Clinical Nutrition*, Mar. 1984, pp. 388–392.

Jenkins, David J. A. et al. "Dietary Fibres, Fibre Analogues, and Glucose Tolerance: Importance of Viscosity" in *British Medical Journal*, May 27, 1978, pp. 1392–1394.

Jenkins, David J. A. et al. "Glycemic Index of Foods: A Physiological Basis for Carbohydrate Exchange," in *The American Journal of Clinical Nutrition*, Mar. 1981, pp. 362–366.

Jenkins, David J. A. et al. "Unabsorbable Carbohydrates and Diabetes: Decreased Post–Prandial Hyperglycemia" in *The Lancet*, Jul. 24, 1976, pp. 172–174.

"Nutrition Recommendations and Principles for People with Diabetes Mellitus" in *Journal of the American Dietetic Association*, May 1994, pp. 504–511.

Parillo, M. et al. "A High–Monounsaturated–Fat/Low Carbohydrate Diet Improves Peripheral Insulin Sensitivity in Non–Insulin Dependent Diabetic Patients" in *Metabolism*, Dec. 1992, pp. 1373–1378.

Peters, Anne L. et al. "Protein and Fat Effects on Glucose Responses and Insulin Requirements in Subjects with Insulin–Dependent Diabetes Mellitus" in *Am J Clin Nutr*, 1993, pp. 555–560.

Raben, Anne et al. "Resistant Starch: The Effect on Postprandial Glycemia, Hormonal Response and Satiety" in *Am J Clin Nutr*, 1994, pp. 544–551.

ENTERAL DIET AND METHOD FOR PROVIDING NUTRITION TO A DIABETIC

This is a continuation-in-part of U.S. patent application Ser. No. 08/051,632, filed Apr. 22, 1993, and entitled: "ENTERAL DIET AND METHOD FOR PROVIDING NUTRITION TO A DIABETIC."

BACKGROUND OF THE INVENTION

The present invention relates generally to compositions and methods of treating diabetes. More specifically, the present invention relates to a method for providing nutrition, or a nutritional supplement, to a patient having diabetes without substantially increasing blood glucose levels.

Diabetes Mellitus is a chronic disorder affecting carbohydrate, fat, and protein metabolism. It is characterized by hyperglycemia and glycosuria resulting from a defect or deficient insulin secretory response. The number of patients diagnosed as diabetic was estimated in 1985 to be 10 million in the United States alone, with the figure increasing at a rate of 6% per year. Two major variants of the disease exist.

One variant, seen in about 10% of all idiopathic diabetics is referred to as insulin dependent diabetes mellitus (IDDM) or juvenile onset diabetes. This variant is frequently manifested for the first time in youth and is characterized by progressive loss of insulin secretory function by beta cells of the pancreas and hence a progressive "dependency" on exogenous insulin for the maintenance of carbohydrate metabolism. (This characteristic is shared by those non-idiopathic, or "secondary" diabetics whose disorder have their origins in pancreatic disease.)

The second variant of idiopathic diabetes is referred to as non-insulin dependent diabetes mellitus (NIDDM) or adult onset diabetes mellitus. This variant accounts for the remainder of the idiopathic diabetic population.

All diabetics, regardless of their genetic and environmental backgrounds or age of onset of the disease, have in common an apparent lack of insulin or inadequate insulin function. Because transfer of glucose from the blood to the muscle and fat is insulin dependent, diabetics lack the ability to utilize glucose adequately. Further, because glycogenolysis is ordinarily inhibited by insulin, the rate of glycogenolysis is elevated in diabetics. Both of these "derangements" from normal metabolic events lead to the accumulation of glucose in the blood (hyperglycemia) to the point where renal glucose reabsorption capacity is exceeded and glycosuria occurs. A major source of energy for the diabetic becomes fatty acids derived from triglycerides stored in fatty tissue.

In the liver, fatty acids are oxidized to ketone bodies which are circulated and used as an energy source by the tissues. In the IDDM patient and sometimes the NIDDM patient, the rate of formation of the ketone bodies may exceed their rate of utilization and ketosis along with metabolic acidosis may occur.

Since tissues appear to be starving for glucose, dietary tissue sources of protein are used in glycogenesis. Anabolic processes such as synthesis of glycogen, triglycerides and proteins are "sacrificed" to catabolic activities including glycogenolysis, gluconeogenesis and mobilization of fats. Thus, the diabetic state which has its origins in a "simple" insulin defect, results in widespread metabolic disturbances having long term pathological effects on nearly all organs and tissues of the body. Indeed, the diabetic state is one of the prime contributors to deaths caused by myocardial infarction, renal failure, cerebrovascular disease, atherosclerotic heart disease, and systemic infections.

The hyperglycemic and glycosuric conditions of the diabetic disease may be treated by a manipulation of the diet, control of body weight, and regulation of physical activity. In some diabetics, particularly those suffering from NIDDM, the hyperglycemic and glycosuric conditions can be treated by oral administration of antihyperglycemic agents such as derivatives of sulfonylureas, sulfonamides, biguanides and other compounds. For diabetics suffering from IDDM and advanced NIDDM, however, therapy has focussed on administration of exogenous insulin.

Of course, the nutritional management of diabetes is of great concern. The American Diabetes Association has published guidelines for nutritional management of diabetes mellitus. These guidelines suggest that sufficient calories be given to a patient to achieve and maintain reasonable weight.

Pursuant to the ADA (1986 Guidelines), the diet may include up to 55%–60%, based on calories, as carbohydrates. The protein content of the diet recommended for people with diabetes in approximately 12%–20% of the total calories. The fat content of the diet is recommended to be less than 30% of the total calories. Of this polyunsaturated fats are recommended up to 10%, saturated fats recommended at less than 10%, and mono-unsaturated fats will make up the remaining percentage of the fat at a range of 10%–15%.

ADA guidelines 1994 revision are more flexible regarding percentage of calories from carbohydrates, but emphasize even further the need for an adequate lipid intake.

In many situations, it may be necessary to support a diabetic patient with an enteral diet or supplement. These diets can either be administered through a nasogastric tube or other external means or provided in a liquid form that the patient drinks. Such formulations may be necessary when patients are hospitalized and/or in other situations where the patients are unable to meet necessary dietary requirements without a nutritional formulation or supplementation.

Presently, a formulation on the market for a diabetic patient is Glucerna® sold by Ross Product Division, Abbott Labs. See U.S. Pat. No. 4,921,877. Glucerna® provides approximately the following macronutrient profile: protein 16.7% of the calories; carbohydrate 33.3% of the calories; fat approximately 50% of the calories. The fat in Glucerna® is provided solely through long-chain triglycerides. Specifically, the fat is provided as 85% of the calories being safflower oil and 15% of the calories being soybean oil. The caloric density of Glucerna® is approximately 1 cal/ml.

The inventors of the present invention do not believe that presently available formulations satisfactorily meet the nutritional needs of the diabetic patient.

SUMMARY OF THE INVENTION

The present invention provides a composition and method for providing nutrition, or a nutritional supplement, to a diabetic patient. Pursuant to the present invention, a moderate to low carbohydrate, high fat enteral formulation is provided. The fat comprises, in part, medium chain triglycerides (MCTs) and has an n- 6:n-3 ratio of preferably not more than 10.

The present invention allows reduced insulin to metabolize the "meal" and reduces the sensitivity to dose and timing of insulin to blunt the post-prandial serum glucose excursion. Additionally, due to the content of the formulation, improvement in the patient's tolerance to the formula is achieved.

To this end, the present invention provides a method for providing nutrition to a diabetic patient without substantially increasing blood glucose levels comprising the steps of enterally administering a composition comprising a protein source, a carbohydrate source, and a fat source that includes medium chain triglycerides and has an n-6:n-3 ratio of not more than 10.

In an embodiment, the composition includes approximately 8 to about 25% of the calories as the protein source.

In an embodiment, the composition includes less than 50% of the calories as the carbohydrate source.

In an embodiment, the composition includes approximately 30 to about 50% of the calories as the fat source. In an embodiment, preferably, the fat source includes long chain triglycerides (LCTs) and the ratio of MCTs to LCTs is approximately 1:4.

In an embodiment, the composition includes dietary fiber.

In an embodiment, the composition includes high amylose starch.

In an embodiment, the fat source of the composition comprises approximately 40% to about 70%, by calories, mono-unsaturated fatty acids.

In an embodiment, the composition includes at least one component chosen from the group consisting of sucrose, fructose, maltose, sorbitol, or xylitol.

In an embodiment, the composition is administered to the diabetic patient through a nasogastric tube.

In an embodiment, the composition is administered as a supplementation or a sole source of nutrition to the diabetic patient.

In an embodiment, the diabetic patient is non-insulin dependent.

In an embodiment, the diabetic patient is insulin dependent.

In an embodiment, the fat source comprises, by calories, at least 4% essential fatty acids.

In an embodiment, the composition provides at least 100% of the U.S. RDA of all vitamins and minerals per 1500 Kcal.

An advantage of the present invention is it provides an improved composition for providing nutritional requirements and/or support to a patient having diabetes.

Furthermore, an advantage of the present invention is that it provides a method for providing nutrition to a patient having diabetes.

Additionally, an advantage of the present invention is that it provides a method and composition for providing nutrition to a diabetic patient without substantially increasing blood glucose levels.

Still further, an advantage of the present invention is that it provides a composition specifically directed to the meet the nutritional requirements and needs of the diabetic patient.

A further advantage of the present invention is to provide a composition that includes, in an embodiment, high amylose starch that is digested at a slower rate than other starches and thereby leads to a reduction in the rate at which glucose enters the blood stream.

Additionally, an advantage of the present invention is that the use of high amylose starch enhances glycemic control in the diabetic patient.

Moreover, an advantage of the present invention is to provide a fat course having an n-6:n-3 ratio that improves immune response.

Furthermore, an advantage of the present invention is to provide a formulation having dietary fiber that will tend to slow down the metabolism of carbohydrates in the formula.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a composition and method for meeting the nutritional requirements of a diabetic patient. Pursuant to the present invention, a composition is enterally administered to the patient. The composition of the present invention is a moderate to low carbohydrate, high fat enteral formulation including a protein source, a carbohydrate source, and a fat source having an MCT content. By reducing the carbohydrate intake and substituting therefor MCTs, the composition reduces the insulin necessary to metabolize the meal. Additionally, the composition reduces sensitivity to dose and timing of insulin to reduce the post-prandial serum glucose excursion. The present invention provides benefits in improved tolerance, metabolic and glucose management/insulin requirements and additional advantages.

An advantage of the present invention is provided by non-glucose, non-insulin dependent alternatives to carbohydrates in an enteral product for diabetes. The present invention avoids disadvantages of many current products and minimizes the increase in blood glucose and the associated insulin requirement which follows feeding of these patients.

In an embodiment, another advantage of the present invention is that it provides a formula including dietary fiber that will slow down the metabolism of the carbohydrates in the formula. Additionally, the use of a high amylose starch in the formula will lead to a reduction in the rate at which glucose enters the blood stream. Because it is resistant to digestion by pancreatic enzymes, the high amylose starch of the composition of the present invention enhances glycemic control in the diabetic patient. An advantage of the formula of the present invention is that it provides a composition having a low carbohydrate content and high amylose starch that is slowly digested.

The fat source preferably comprises approximately 30% to about 50% of the total calories of the composition. In a preferred embodiment, 30% to about 44% of the calories are derived from the fat source. The fat source comprises long chain triglycerides (LCTs) and medium chain triglycerides (MCTs).

MCTs can be a mixture of C6–C12. For example, MCTs can be a mixture of C6:0(1–2%), C8:0(65–75%), C10:0(25–30%), and C12:0(1–2%). In an embodiment, the MCTs comprise 20% of the fat source and LCTs comprise 80% of the fat source.

The use of MCTs aids in digestion. Digestion of MCTs may be easier than LCTs in that LCTs are digested by various lipases; in contrast to LCTs, pancreatic lipase is not essential to digestion of MCTs. Additionally, absorption of MCTs is faster as compared to LCTs. LCTs require incorporation into chylomicron by intestinal mucosal cells. Similarly, transport of MCTs is via portal circulation directly to the liver whereas LCTs are transported via lymphatics and systemic circulation before finally ending up in the liver.

LCTs are oxidized more slowly requiring carnitine for entry into the mitochondria. The source of MCTs can comprise fractionated coconut oil.

Preferably, the LCTs are provided as canola oil, olive oil, and hi-oleic safflower oil. Although other oils can be used such as, e.g., soy oil, high-oleic sunflower oil, or any oil rich in mono-unsaturated fatty acid (MUFA). These oils not only provide linoleic acid, an essential fatty acid, but also provide n-3 fatty acids. Linolenic acid, the predominate n-3 fatty acids supplied by these oils, may serve as a precursor to other n-3 fatty acids which have anti-inflammatory activity. Preferably, at least 4%–10%, by calories, essential fatty acids are provided by the composition of the present invention.

Preferably, in an embodiment, the ratio of n-6:n-3 fatty acids is approximately 4. However, other ratios can be used with preferably the ratio of n-6:n-3 being 2 to 10. This lower ratio improves the immune response.

Additionally, the fat source comprises approximately 40% to about 70% of the total calories as mono-unsaturated fatty acids (MUFA). In a preferred embodiment, the MUFA content of the fat is approximately 58% by caloric content. This higher level of MUFA as part of a high fat/moderate carbohydrate diet provides lower serum lipids than a lower fat diet that does not contain a significant amount of MUFA. An advantage of the composition of the present invention is that it provides a high fat diet with MCTs and a high content of MUFAs.

Pursuant to the present invention, preferably the composition provides 8 to about 25% of the total calories as a protein. Preferably, the formulation contains caseinate, whey protein, or non-fat milk as the protein source.

Preferably the composition comprises approximately 30 to less than 50% in total calories as a carbohydrate and most preferably approximately 40% as a carbohydrate. A variety of carbohydrates can be utilized such as maltodextrins or other complex polysaccharides. If desired, the carbohydrates can be substituted for, in part, by fructose, sucrose, maltose, sorbitol or xylitol. This will provide non-glucose, non-insulin dependent alternatives which provide carbon skeletons to be used as an energy source.

Preferably, the carbohydrate component will comprise in part starch. Preferably, the composition will include a high amylose starch. A high amylose starch provides advantages over, for example, an acid modified starch. A high amylose starch will break down much more slowly than an acid modified starch and is digested more slowly as well. This leads to a reduction in the rate at which glucose enters the blood stream.

In a preferred embodiment, the high amylose starch will consist of approximately 25 to about 75% amylose and approximately 25% to about 75% amylopectin. In a most preferred embodiment, the amylose starch will consist of approximately 70% amylose and approximately 30% amylopectin.

In a preferred embodiment, the high amylose starch will comprise approximately 1% to about 5% of the composition; approximately 10 to 50 g/L of the composition. In a most preferred embodiment, the high amylose starch will comprise approximately 2.1% (23 g/L) of the composition.

Additionally, the composition, in a preferred embodiment, will include dietary fiber. The addition of dietary fiber to the formula tends to slow down the metabolism of the carbohydrates in the formula. Preferably, the composition includes approximately 8 grams to about 25 grams per liter of the composition as dietary fiber.

The dietary fiber will preferably include both soluble and insoluble fiber. Preferably, the soluble fiber will comprise approximately 50 to about 75% of the fiber present. In a most preferred embodiment, the soluble fiber will comprise approximately 70% and the insoluble fiber will comprise 30% of the total fiber content.

Preferably, the formulation will provide 100% of the U.S. RDA in 1500 kcal of all vitamins and minerals. Additionally, preferably, the present invention provides 1.0–1.5 kcal/ml.

The composition can include a surfactant. A variety of surfactants can be used such as egg yolk phospholipids, soy phospholipids, and milk phospholipids.

By way of example and not limitation, an example of the present invention will now be given. The formulation is intended for a diabetic patient. The formulation can be fed by mouth or by tube or can be used as a supplement or as a complete diet.

EXAMPLE

| Nutrient | Source | Unit | US Diabetic (Per Liter) |
|---|---|---|---|
| Caloric Density | | Kcal/ml | 1.0 |
| Protein | (18% Cal) | g | 45 |
| | Caseinates | g | 45 |
| Fat | (42% Cal) | g | 50 |
| | MCT | g | 10 |
| | Canola oil | g | 18.5 |
| | Hi-Oleic Safflower | g | 18.0 |
| | Soy Lecithin | g | 3.5 |
| | n-6:n-3 ratio | | 3.5 |
| | MCT/LCT = 20/80 | | |
| CHO | (40% Cal) | g | 100 |
| | Maltodextrin | g | 45 |
| | High amylose starch | g | 23 |
| | Fructose | g | 22 |
| | Pectin | g | 3 |
| | Soy fiber | g | 5 |
| | Gum Arabic or guar | g | 7 |
| Dietary Fiber | | g | 15 |
| Flavoring | | | Vanilla |
| Lactose | | | Lactose free |
| Vitamin A | | IU | 4000 |
| Beta-carotene | | mg | 2 |
| Vitamin D | | IU | 320 |
| Vitamin E | | IU | 30 |
| Vitamin K | | mcg | 50 |
| Vitamin C | | mg | 140 |
| Folic Acid | | mcg | 400 |
| Thiamine | | mg | 2 |
| Riboflavin | | mg | 2.4 |
| Vitamin B6 | | mg | 4 |
| Vitamin B12 | | mcg | 8 |
| Niacin | | mg | 28 |
| Biotin | | mcg | 300 |
| Pantothenate | | mg | 14 |
| Choline | | mg | 400 |
| Calcium | | mg | 720 |
| Phosphorus | | mg | 720 |
| Magnesium | | mg | 286 |
| Iodine | | mcg | 120 |
| Manganese | | mg | 3 |
| Copper | | mg | 1.5 |
| Zinc | | mg | 15 |
| Iron | | mg | 12.8 |
| Sodium | | mg | 740 |
| Potassium | | mg | 1400 |
| Chloride | | mg | 1200 |
| Selenium | | mcg | 75 |
| Chromium | | mcg | 125 |
| Molybdenum | | mcg | 200 |
| Carnitine | | mg | 100 |
| Taurine | | mg | 100 |
| M-Inositol | | mg | 800 |

| Nutrient | Source | Unit | US Diabetic (Per Liter) |
|---|---|---|---|
| | Comments | | |
| Osmolality: | 425 mOsm/kg water max. | | |
| Viscosity: | 90 CPS max. | | |
| Packaging: | cans or bags | | |
| Processing: | UHT aseptic or Retorting | | |

By way of comparison, a comparison of the diabetic formula of the present invention vis-a-vis Glucerna® from Ross is set forth below.

| | | Present Invention | Ross Glucerna® | Comments | |
|---|---|---|---|---|---|
| Caloric Density: | Kcal/mL | 1 | 1.06 | | |
| Caloric Distribution: | | | | ADA Guideline (1986) | ADA Guideline (1994) |
| Protein | % | 18 | 16.7 | 12–20 | 10–20 |
| Fat | % | 42 | 50 | <30 (<10% saturated) | <10% saturated |
| CHO | % | 40 | 33.3 | 55–65 | |
| Protein Composition: | | | | | |
| Total Protein | g/L | 45 | 41.8 | 100% Casein | 100% Casein |
| Fat Composition: | | | | | |
| Total Fat | g/L | 50 | 55.7 | | |
| MCT | g/L | 10 | 0 | MCT/LCT = 20/80 Canola | No MCT Soy |
| LCT | g/L | 40 | 55.7 | hi-oleic safflower | hi-oleic sallower |
| Fatty Acids Profile: | | | | | |
| MCT | % | 18 | 0 | 7.6% of TEI | 0% of TEI |
| LCT | | | | | |
| Saturated | % | 7.6 | 11.2 | 3.3% of TEI | 5.6% of TEI |
| Mono-Unsaturated | % | 57.8 | 76.1 | 58% of fat calories | 76% of fat calories |
| Poly-Unsaturated | % | 17.1 | 12.7 | | |
| n6:n3 Ratio | | 3.5 | 14 | | |
| EFA | % | 7.2 | 7.1 | EFA:7.2% of TEI | EFA:7.1% of TEI |
| Carbohydrate Composition: | | | | | |
| Total CHO's | g/L | 105 | 93.7 | | Total includes all fibers |
| Total available CHO's | g/L | 100 | 83.3 | | |
| High amylose Starch | g/L | 23 | 0 | Resistant to digestion | Contains no starch |
| Maltodextrin | g/L | 45 | 44.4 | | |
| Fructose | g/L | 22 | 17.7 | | |
| Soluble fibers | g/L | 10 | 0.75 | | |
| Insoluble fibers | g/L | 5 | 13.65 | | |
| Lactose | | | | Lactose-free | Lactose-free |
| Dietary Fiber Composition: | | | | | |
| Total D. Fibers | g/L | 15 | 14.4 | Soluble: Insoluble = 2:1 | 95% insoluble |
| Pectin | g/L | 3 | — | Note: soluble fiber slows ↓ digestion | |
| Gum Arabic | g/L | 7 | — | | |
| Soy fiber | g/L | 5 | 14.4 | | |
| Vitamins: Meet 100% USRDA's in Kcals: | | 1400 | 1422 | | |
| Minerals: Meet 100% USRDA's in Kcals: | | 1400 | 1422 | | |
| Trace Nutrients include Cr, Mo, Se, Taurine, Carnitine, m-inositol | | | | | |
| Chromium: | mcg/L | 125 | 124 | "Cr" improves | |

-continued

|  | Present Invention | Ross Glucerna ® | Comments |
|---|---|---|---|
|  |  |  | glucose tolerance |
| Flavoring | Vanilla | Vanilla |  |
| Taste | Sl. sweet | Sl. sweet |  |
| Osmolality | 400 | 375 |  |

By way of example, and not limitation, a contemplative example of the use of the formulation will now be given.

CONTEMPLATIVE EXAMPLE

A 45 year old insulin dependent diabetic female patient is admitted to the Intensive Care Unit with severe head trauma and multiple other injuries following an auto accident. She is unconscious and will require tube feeding of an enteral formula to meet her basic and stress nutritional needs. Standard enteral tube feeding formulas with only maltodextrin will produce high levels of blood glucose, increase insulin requirements, and make her diabetes hard to control during her recovery from the accident. Standard formulas with only long chain triglycerides are less well tolerated, absorbed less well, and metabolized more slowly.

Instead of a standard enteral tube feeding formula, she is administered by tube the formula of the present invention. The formula is administered until the patient can satisfy her caloric requirements through a normal diet.

The high amylose starch and medium chain triglycerides of this invention serve to blunt the increase of blood sugar and make her diabetes easier to control. In addition, the MCTs are more easily and rapidly absorbed, and are better transported, metabolized, and utilized as an energy source with better gastrointestinal tolerance, all of which are of a significant benefit to this type of patient.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for providing nutrition to a diabetic patient without substantially increasing blood glucose levels comprising the steps of enterally administering to the diabetic patient a low carbohydrate, high fat enteral composition comprising:

a protein source;

a carbohydrate source including a slowly digested high amylose starch component; and a fat source that includes medium chain triglycerides and has an n-6:n-3 ratio of not more than 10.

2. The method of claim 1 wherein approximately 8 to about 25% of the calories of the composition are provided as the protein source.

3. The method of claim 1 wherein less than 50% of the calories of the composition are provided as the carbohydrate source.

4. The method of claim 1 wherein approximately 30 to about 44% of the calories of the composition are provided as the fat source.

5. The method of claim 1 wherein the composition includes from about 1% to about 5% of high amylose starch based on the overall composition.

6. The method of claim 5 wherein the high amylose starch includes approximately 25 to about 75% amylose and approximately 25% to about 75% amylopectin.

7. The method of claim 1 wherein the fat source comprises approximately 40 to 70% mono-unsaturated fats.

8. The method of claim 1 wherein the composition further comprising dietary fiber.

9. The method of claim 8 wherein the dietary fiber includes both soluble and insoluble dietary fiber.

10. A method for providing nutrition to a diabetic patient comprising the steps of enterally administering to the diabetic patient a composition that comprises:

a protein source that provides at least about 8% of the total calories of the composition;

a carbohydrate source that provides less than about 50% of the total calories of the composition, the carbohydrate source including a slowly digested high amylose starch; and a fat source that provides at least 30% of the total calories of the composition, including medium chain triglycerides (MCTs) and having an n-6:n-3 ratio of 10 or less.

11. The method of claim 10 wherein the fat source includes at least one oil selected from the group consisting of olive oil, canola oil, hi-oleic safflower oil, and hi-oleic sunflower oil.

12. The method of claim 10 wherein the composition is administered to the diabetic patient through a nasogastric tube.

13. The method of claim 10 wherein the composition is administered as a supplementation to the diabetic patient.

14. The method of claim 10 wherein the diabetic patient is non-insulin dependent.

15. The method of claim 10 wherein the fat source includes long chain triglycerides (LCTs) and the ratio of MCTs to LCTs being approximately 1:4.

16. The method of claim 10 wherein the fat source comprises approximately 30% to 70%, by calories, mono-unsaturated fatty acids.

17. The method of claim 10 wherein the high amylose starch comprises from about 1% to about 5% of the overall composition.

18. The method of claim 10 wherein the composition provides dietary fiber.

19. The method of claim 18 wherein the dietary fiber includes both soluble and insoluble dietary fiber.

20. A method for providing nutrition to a patient with diabetes without increasing blood glucose levels comprising:

enterally administering to the patient with diabetes an effective amount of a composition comprising a protein source, a carbohydrate source that includes high amylose starch, a fat source including a mixture of medium and long chain triglycerides wherein the fat source comprises approximately 30% to 70%, by calories, mono-unsaturated fatty acids, and dietary fiber.

* * * * *